United States Patent [19] [11] 4,198,853
Graham et al. [45] Apr. 22, 1980

[54] POROSITY MEASUREMENT

[75] Inventors: John F. Graham, Perivale; Donald Hardy, Wembley, both of England

[73] Assignee: American Filtrona Corporation, Richmond, Va.

[21] Appl. No.: 956,843

[22] Filed: Nov. 2, 1978

[30] Foreign Application Priority Data

Nov. 4, 1977 [GB] United Kingdom ............... 46099/77

[51] Int. Cl.² ............................................. G01N 15/00
[52] U.S. Cl. ........................................... 73/38; 73/159
[58] Field of Search .................................... 73/38, 37.7

[56] References Cited

U.S. PATENT DOCUMENTS

| 2,755,660 | 7/1956 | Kammermeyer et al. | 73/38 |
| 2,861,451 | 11/1958 | Emmons | 73/38 |

FOREIGN PATENT DOCUMENTS

| 640387 | 4/1962 | Canada | 73/38 |
| 435171 | 10/1926 | Fed. Rep. of Germany | 73/38 |
| 1063832 | 8/1959 | Fed. Rep. of Germany | 73/38 |

*Primary Examiner*—Gerald Goldberg
*Assistant Examiner*—Joseph W. Roskos
*Attorney, Agent, or Firm*—Holman & Stern

[57] ABSTRACT

The present invention provides a method and apparatus for evaluating the porosity of a sheet material at a given value of gas flow or pressure drop (PD), with account being taken of the following relationship between the parameters of flow and PD:

$$\text{Flow} = A\,(PD)^N,$$

in which one of the parameters is set at a number (e.g. 3) of values close to the said required value, the other parameter is measured at each, the values of A and N for the sample under test are calculated therefrom, and then the precise gas flow (or PD) at the given PD (or gas flow), and hence the porosity, is calculated from the said relationship. The automatic setting, and the calculations, are effected by means of a microprocessor.

17 Claims, 15 Drawing Figures

POROSITY MEASUREMENT

This invention relates to the measurement of porosity (gas permeability), especially porosity of sheet material such as paper.

The porosity of a sheet is a measure of the ease with which gas (usually air) will flow transversely through the sheet and is usually expressed in terms of units of gas flow/unit sheet area/unit pressure drop across the sheet, e.g. in units of ml/min/sq.cm./100 mm Wg pressure drop. A porosity value may be obtained from the measured gas flow across the sheet at a fixed pressure drop, or from the measured pressure drop at a fixed gas flow.

Figure 1:
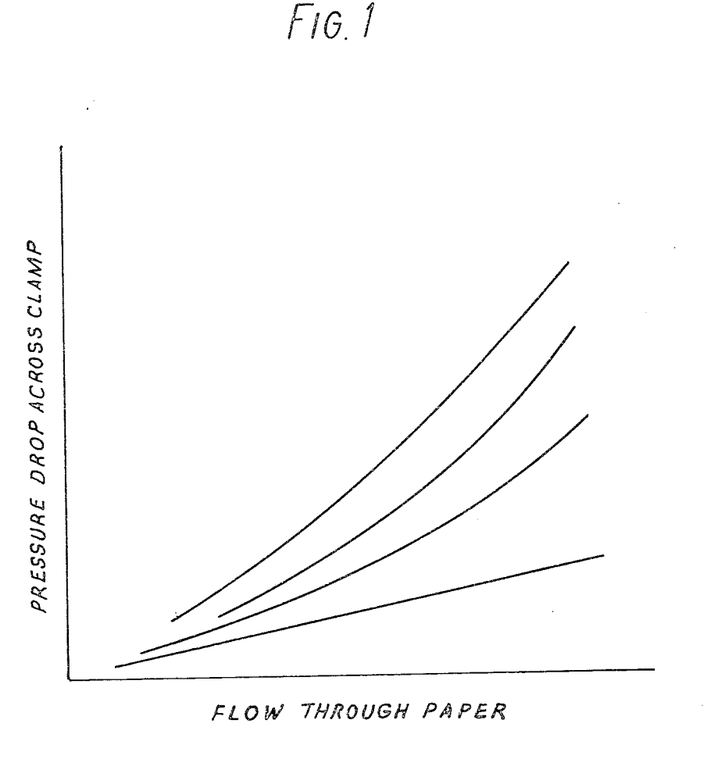
FIG. 1 is a graph of typical flow rates versus pressure drop across different sheet materials.

Quoted porosity values for sheet material have not been readily and reliably comparable heretofore, because the value obtained can vary with the shape and area of the clamp used and with the conditions under which the measurements are taken. We have found for air flow through paper that flow and pressure drop (PD) are not related simply in direct proportion. Tests on a wide range of papers show that the relationship is:

$$\text{flow } F = A(PD)^N$$

where A and N are constants for each paper but vary from paper to paper, depending on its porosity. This is illustrated in the graph of FIG. 1 which shows PD versus flow curves for several papers having different respective porosities.

The present invention provides a method and apparatus for porosity evaluation which takes account of the varying flow/PD relationship and allows more ready and reliable comparison between independently obtained porosity values.

In the method and apparatus according to the invention, instead of setting one of the parameters (flow or PD) at its single fixed required value and measuring the other at this value, the said one parameter is automatically set sequentially at a number (e.g. 3) of values near to the said required value, the other parameter is measured at each, and from these readings the values of A and N are ascertained for the sample under test in the region of the said required value of the one parameter. From this there is calculated the precise flow (or PD) at the exact required PD (or flow), and hence the porosity.

According to a first aspect of the present invention there is provided a method of measuring the porosity of a sheet material to a gas at a given flow rate of the gas through the sheet material which comprises automatically setting the flow rate of the gas through the sheet material at a number of values close to said given value, measuring the value of the pressure drop through the sheet material at each of said close flow rate values, calculating from said close and measured values the values of A and N in the equation:

$$\text{flow rate} = A \times (\text{pressure drop})^N;$$

from these calculated values of A and N for the sheet material calculating the pressure drop through the material at said given flow rate, and calculating the porosity with the given flow rate and the calculated pressure drop, the automatic setting of the flow rate at said close values, the calculation of A and N, and the calculation therefrom of the pressure drop at the given flow rate and the porosity being achieved by means of a microprocessor.

According to a second aspect of the invention there is provided a method of measuring the porosity of a sheet material to a gas at a given pressure drop of the gas through the sheet material which comprises automatically setting the pressure drop of the gas through the sheet material at a number of values close to said given value, measuring the value of the flow rate through sheet material at each of said close pressure drop values, calculating from said close and measured values the values of A and N in the equation:

$$\text{flow rate} = A \times (\text{pressure drop})^N;$$

from these calculated values of A and N for the sheet material calculating the flow rate through the material at said given pressure drop, calculating the porosity with the given pressure drop and the calculated flow rate, the automatic setting of the pressure drop at said close values, the calculation of A and N, and the calculation therefrom of the flow rate at the given pressure drop and the porosity achieved by means of a microprocessor.

According to a third aspect of the invention there is provided apparatus for use in measuring the porosity of a sheet material to a gas at a given flow rate or pressure drop through the sheet material, which apparatus comprises clamp means for holding at least a portion of the sheet material and defining a gas flow path therethrough of predetermined area, a controllable gas source, means defining a gas flow route from the controllable gas source to the clamp means, and transducing means operable to sense the gas flow rate in the gas flow route and the pressure drop across the clamp.

According to a fourth aspect of the invention, there is provided apparatus of said third aspect, wherein a microprocessor is operatively connected to the controllable gas source and transducing means and operable automatically to set the flow rate of the gas or the said pressure drop number of values close to said given value, to calculate from the said close values and the corresponding sensed values of the pressure drop the values of A and N in the equation:

$$\text{flow rate} = A \times (\text{pressure})^N;$$

and to calculate from these calculated values of A and N the corresponding pressure drop or flow rate at said given value, and the porosity with the given value and the calculated flow rate or pressure drop.

In a preferred embodiment of the apparatus, a gas flow restrictor is provided in the gas flow route, this restrictor having a known relationship of gas flow therethrough to pressure drop therethrough. The transducing means is arranged for sensing the pressure drop across the restrictor and across the clamp. A microprocessor is operatively connected to the controllable gas source and to the transducing means and is operable to automatically set the controllable gas source to provide a gas flow in the flow route or a pressure drop across the clamp at a number of values close to a given value at which the porosity of the sheet material to the gas is to be measured. The microprocessor is programmed to calculate flow values from the sensed pressure drop values across the restrictor and the known gas flow to pressure drop relationship of the restrictor, and to calculate from the flow values and clamp pressure drops thus obtained the values of A and N in the equation flow rate=$A \times$(pressure drop)$^N$. The microprocessor is preferably further programmed to calculate the flow rate or pressure drop corresponding to the said given value, using the values of A and N previously calculated, and to thereafter calculate the required porosity.

Preferred embodiments of the present invention will now be described, by way of example, with reference to the accompanying drawings in which.

Figure 2:
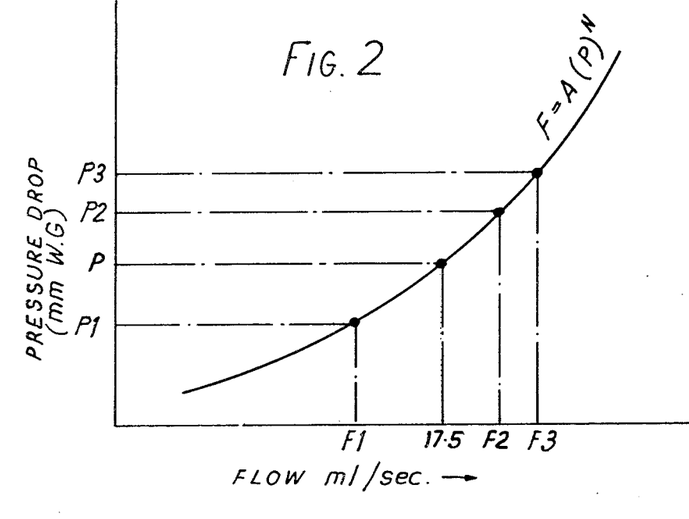
FIGS. 2 and 3 are graphs of pressure drop against flow rate through a piece of paper.
Figure 3:
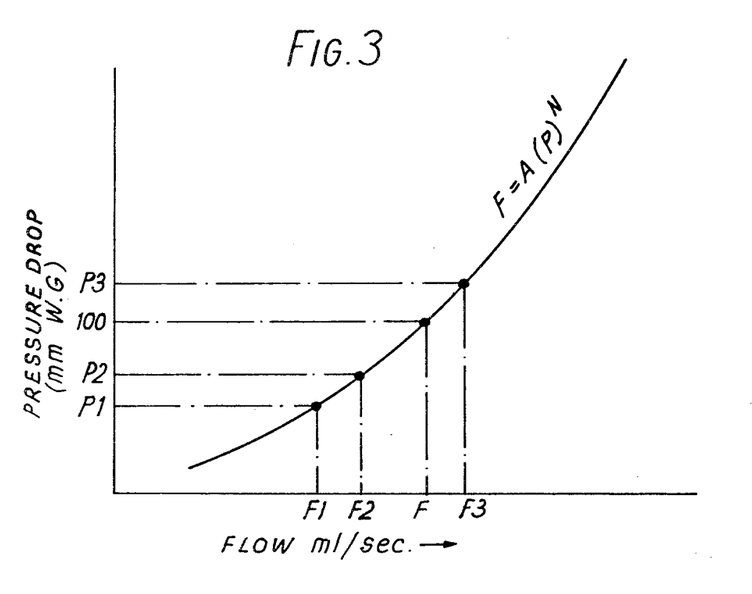

The graphs of FIGS. 2 and 3 illustrate the procedure. Thus, as illustrated in FIG. 2, if it is required to measure porosity at a set flow of 17.5 ml/sec, the flow is set at three trial points $F_1$, $F_2$ and $F_3$ near to the value of 17.5 ml/sec and the corresponding PD's $P_1$, $P_2$ and $P_3$ are measured. From these three pairs of values the values of A, N in the relationship:

$$F = AP^N$$

are calculated; knowing A and N the pressure drop at the required flow rate of 17.5 ml/sec. is calculated from the equation, and the porosity is thence expressed in whatever units are required.

FIG. 3 illustrates the converse case of measuring the porosity at a set pressure difference of 100 mm Wg. The flow is measured at three pressure drop values close to 100 mm Wg; the results are used to calculate A and N and the flow at precisely 100 mm Wg pressure drop is than calculated by substitution in the equation.

The automatic setting of the pressure drop or flow at values adjacent to the required value, the measurement of the second parameter at these values, the calculation of A and N and the calculation therefrom of the porosity at the required value, is achieved by means of a built in microprocessor, which also displays and/or prints out the obtained porosity value. The clamp in which the test sample is held is preferably mountable so as to be replaceable by another. Any one party would then be able to set the device with its own clamp, obtain porosity values in their own units, and then by resetting, to compare the value obtained with those obtained by other laboratory methods.

Figure 4:
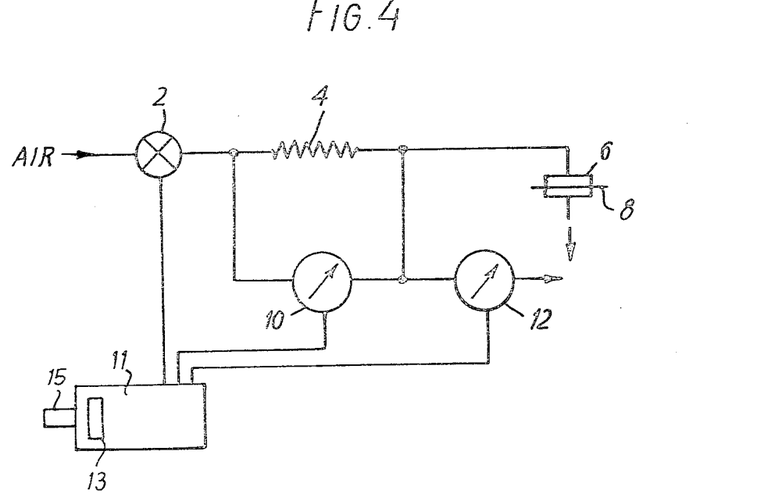
FIG. 4 is a diagrammatic representation of a first apparatus embodying the invention.
Figure 5:
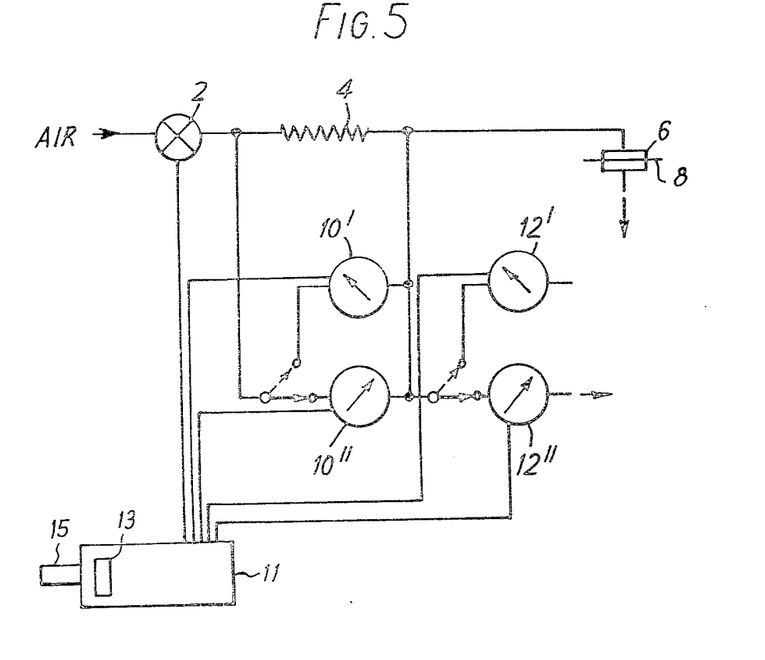
FIG. 5 is a diagrammatic representation of a second apparatus embodying the invention.

Apparatus for using the procedure according to the invention is illustrated diagrammatically and by way of example in FIGS. 4 and 5, wherein like parts are indicated by like reference numerals. In FIG. 4, air from a controllable pressure source 2 passes via fixed restrictor 4 to and through a clamp 6 holding the sheet 8 under test. The fixed restrictor 4 has a linear relationship of flow to PD, i.e. flow=PD/resistance; the value of the resistance being known, measurement of the PD across it allows direct calculation of the flow. The PD across the restrictor and across the clamp is sensed by pressure transducers 10 and 12 respectively, these transducers and the pressure source control being connected to a microprocessor 11 having a display panel 13 or a printout device 15. In a modification of the FIG. 4 arrangement, the transducers 10 and 12 would be replaced by a single transducer switched by a valve from one configuration to the other.

The FIG. 5 arrangement is similar to that of FIG. 4, except that the single transducer 10 is replaced by a high sensitivity transducer 10' and a low sensitivity transducer 10'', transducer 12 likewise being replaced by high and low sensitivity transducers 12' and 12''. The high or low sensitivity transducers are used according to the value of the pressure drop at which the porosity is to be obtained. Once again the two pairs of transducers shown in FIG. 5 could be replaced by a single pair switchable between the two configurations by means of a valve.

The pressure source 2 of FIG. 4 or FIG. 5 could be a motorized regulator and would be driven under the control of the microprocessor 11 to give several values of flow or PD near to the single required value. The microprocessor would then calculate the line of best fit through the various pairs of values for flow and PD obtained, and calculate therefrom the values of A and N. The microprocessor would then calculate the porosity value at the required value of flow or PD and display this at 13 or print it out at 15.

Figure 6:
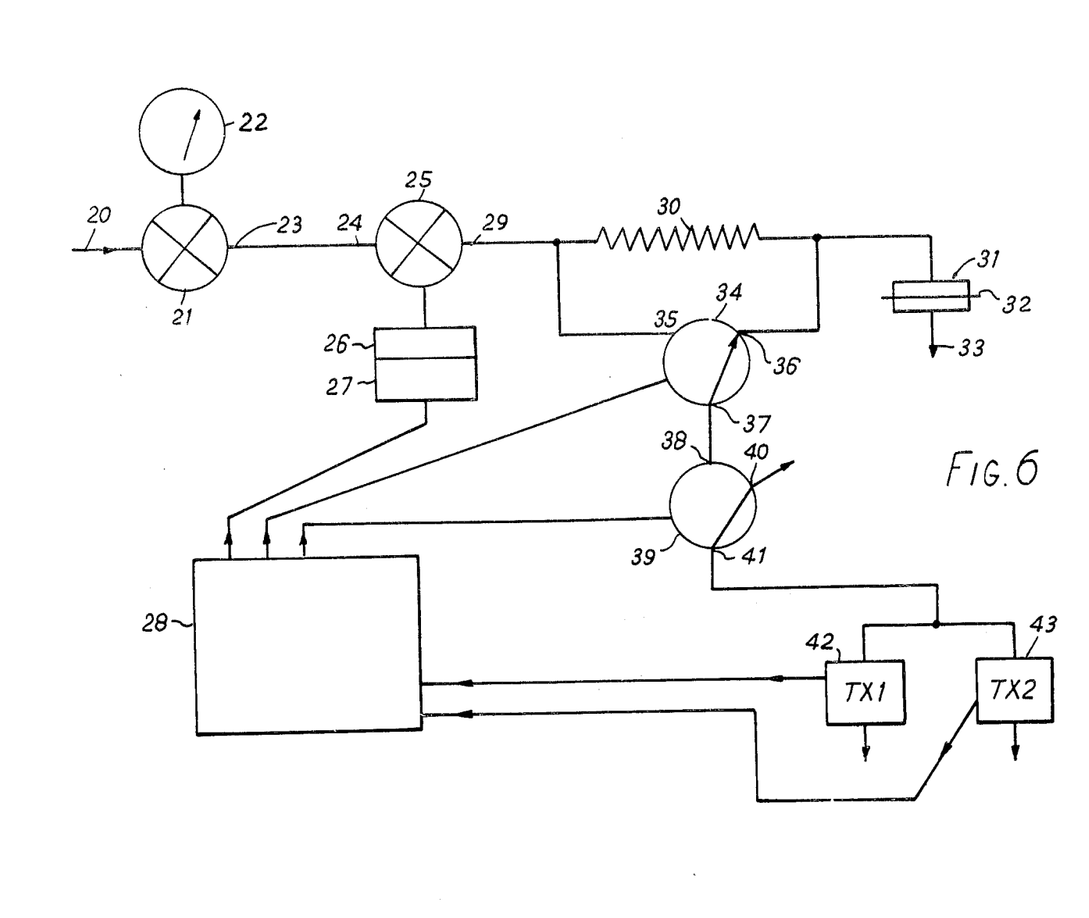
FIG. 6 is a diagrammatic representation of a third apparatus embodying the invention.

Referring now to FIG. 6, a porosity measuring apparatus is shown which has a main air supply inlet conduit 20 connected to supply air to a manually operable pressure regulator 21 equipped with a pressure gauge 22 to enable the output pressure of the pressure regulator 21 to be displayed. The outlet 23 of the pressure regulator 21 communicates directly with the inlet 24 of a flow regulator 25. The flow regulator 25 is operably connected to a step-down gear system 26 which couples the drive shaft of a reversable electric motor 27 to the flow regulator 25. The energization and direction of rotation of the motor 27 is controlled by a microprocessor system 28. The outlet 29 of the flow regulator 25 communicates directly with one end of a linear flow restrictor 30, the other end of which communicates directly with a clamp 31 holding a sheet 32 of paper under test. Air which passes through the paper 32 is vented to atmosphere at 33.

A first electrically controlled two-way valve 34 has one switchable port 35 communicating directly with that end of the restrictor 30 which communicates with the flow regulator 25; and the other switchable port 36 communicating directly with the other end of the restrictor 30. Switching of the valve 34 is controlled by the microprocessor system 28. The fixed port 37 of the valve 34 is in direct communication with one switchable port 38 of a second two-way electrically controlled valve 39, the other switchable port 40 of which is vented to atmosphere. The fixed port 41 of the valve 39 communicates directly with a high sensitivity differential pressure transducer 43, the two transducers being connected in parallel and both venting to atmosphere. The transducers 42 and 43 produce electrical signals representative of the difference between the pressure supplied thereto and atmosphere. These signals are supplied to the microprocessor system 28. The zero points of the two transducers 42 and 43 are initially set with the valve 39 switched as shown in FIG. 6 so that the pressure supplied to the two transducers 42 and 43 by the valve 39 is atmospheric pressure at the port 40 of the valve 39. The microprocessor system 28 carries out this zero reading as a first step.

Before any measurements are taken by the microprocessor system 28, the air pressure at the outlet 23 of the pressure regulator 21 is manually adjusted to a suitable value which is indicated by the pressure indicator 22.

The microprocessor system 28 then switches the valve 39 to bring the ports 41 and 38 thereof into direct communication with one another. With the valve 34 in the condition shown in FIG. 6, the microprocessor system 28 is then able to measure the pressure at the end of the restrictor 30 which is in communication with the clamp 31. By suitably driving the motor 27, the microprocessor system 28 can control the flow regulator 25 so as to bring the pressure at the clamp 31 into a suitable range for measurements to be taken. By switching the valve 34 to bring the ports 37 and 35 thereof into direct communication, the microprocessor system 28 can obtain a measurement of the pressure at that end of the restrictor 30 which is communicating with the outlet 29 of the regulator 25. The pressure readings taken by the microprocessor system 28 are, of course, relative to atmosphere. However, by subtracting the two values obtained from opposite ends of the restrictor 30, the microprocessor system 28 can calculate by simple subtraction the actual pressure difference between the end of the restrictor 30. The retrictor 30 is a linear restrictor, at least within the range of flows and pressure differences encountered in the apparatus of FIG. 6, and consequently the flow to the clamp 31 can be calculated by the microprocessor system 28 which makes use of the pneumatic equivalent of Ohm's law.

The second pressure measurement made by the micro-processor system 28 also gives the pressure difference across the paper 32 in the clamp 31 for the flow producing that pressure difference.

The micro-processor system 28 is prorammed to carry out in the range of flows and pressure differences of interest, e.g. three sets of measurements as described hereinbefore whereby the micro-processor obtains three sets of flow and corresponding pressure difference for the paper 32 in the clamp 31. The micro-processor system 28 is programmed to utilize these three values to find the best values of A and N for generating a curve to fit these three sets of values and then to calculate either the flow corresponding to a particular value of pressure difference on this curve, or to calculate the pressure difference corresponding to a particular value of flow on this curve. The particular value of flow or pressure difference and the corresponding calculated pressure difference or flow are then inserted by the micro-processor system 28 into a formula for calculating porosity and the porosity for the paper 32 is calculated using this formula and the result displayed and printed out.

The pressure regulator 21 may be a Monostat type 10-A PL plunger operated pressure regulator obtainable from John Watson & Smith Ltd., 33, Cliff Road, Leeds, LS6 2EU, Yorkshire, England. The pressure indicator 22 may be a Fairchild pressure gauge obtainable from Deltech Engineering Limited of Albert Drive, Sheerwater, Woking, Surrey, England, or from Fairchild Industrial Products Division, 151, Fairchild Drive, Winston, Salem N.C. 27105, U.S.A. The flow regulator 25 may be a Brooks Elf flow controller, model 8744, which is obtainable from Brooks Instruments, of Hempshaw Lane, Stockport, Cheshire, England. The linear restrictor 30 may be a celanese multi-capillary pressure drop standard, obtainable from British Celanese Limited, England. The valves 34 and 39 are standard electrically controlled air valves. The pressure transducers 42 and 43 may be low pressure transducers of the type FC040 available from Furness Controls Limited, of Beaching Road South, Bexhill-on-Sea, Sussex, England, TN39 3LJ.

In operation, both transducers 42 and 43 sense pressure continuously, but the micro-processor system 28 only makes use of the reading from one or the other of the two transducers according to which one will give the most accurate reading in view of the differential pressure to which it is being subjected.

The electric motor 27 may be a 24 volt AC reversing motor type No. 82-472 obtainable from Crouzet Limited, of 108, Hawley Lane, Farnborough, Hampshire, England. This is a triac controlled motor with two windings.

Figure 7:
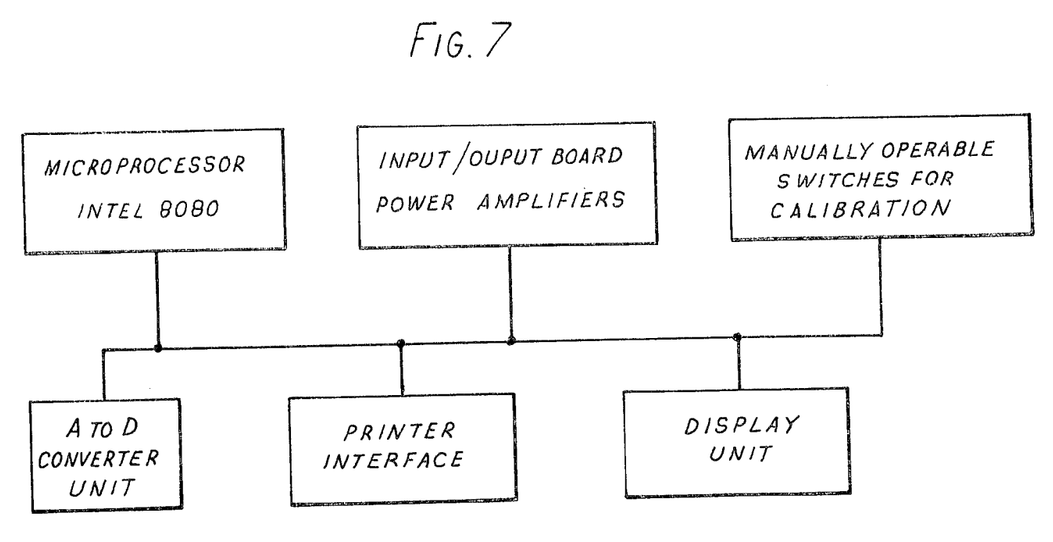
FIG. 7 is a block diagram of a microprocessor system of the apparatus of FIG. 6.

FIG. 7 shows the micro-processor system 28. The processing part of this sytem is, e.g. an Intel 8080 microprocessor system as obtainable from Intel Corporation, 3065 Bowers Avenue, Santa Clara, Calif. 95051, U.S.A.

Since it is necessary to be able to calibrate the system, certain variables need to be fed into the micro-processor system. To do this, a set of manually pre-settable on/off switches is provided. These switches can subsequently be read by the processor whenever the appropriate factors are required.

Each of the transducers 42 and 43 produces an output voltage which ranges over the range 0 to 1 volts in response to the full range of pressure to which it is subjected. The output voltages of the two transducers are fed to an A to D converter, e.g. analogue devices AD 7550BD, which is a plus and minus two volts twelve bit device. This analogue digital converter is interfaced to an Intel 8255 input/output chip which directly interfaces the A/D device to a data bus of the Intel 8080 micro-processor system.

To control the two valves 34 and 39, the motor 27, an input/output board with power amplifier is provided. The input/output board includes medium power transistors and triacs and these devices are coupled to output ports of an Intel 8255 chip which interfaces the board to the micro-processor. The board also has pushbuttons and switches to enable the user to instruct the micro-processor system 28 and these pushbuttons and switches are coupled to input ports of the 8255 chip. It should be noted that the ports of the 8255 chip are address controllable so that inputs/outputs can be read and written in accordance with the programme.

The system 28 includes a dot matrix printer which is controlled by the printer interface unit which compises a pattern generator and a first in first out memory, for storing one line of print at a time. This fifo is interfaced with the 8080 micro-processor by a 8255 input output chip.

The display unit has four decades of readout to enable the results obtained by the micro-processor system to be read. The display drivers are interfaced by another 8255 to the 8080 micro-processor.

Figure 8:
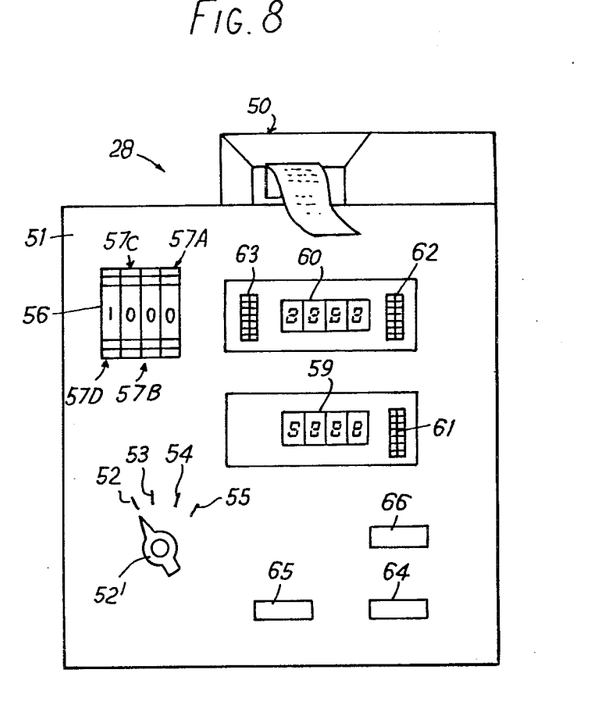
FIG. 8 is a somewhat schematic representation of a first view of the microprocessor system of FIG. 6, and FIGS. 9(a), (b) and (c) and 10(a), (b), (c) and (d) are flow diagrams of calibrate and measurement modes of operation of the microprocessor system of FIG. 6.

FIG. 8 shows somewhat schematically the front view of the micro-processor system 28. The printer 50 is mounted above the front panel 51 Mounted in the front panel 51 are a multi-way switch 52′ in this case a a four-way switch, which is manually settable in any one of four positions indicated on the front panel by markings 52 to 55, a clamp area display switch 56 with segments 57 A,B,C,D, a clamp pressure display 59, a flow display 60, three sets of manually settable switches 61, 62 and 63, a ready pushbutton 64, a calibrate pushbutton 65, and a start pushbutton 66.

When a measurement is to be taken, the user first pushes the pushbutton 64 to set the system 28 in its ready condition. The pushbutton 65 is not used except during calibration procedures. For measurement, the start pushbutton 66 is pushed to set the system 28 in its start condition. The system will then interrogate the pushbutton 65 and, on finding that it has not been actuated, proceed to the beginning of a measurement programme. The system first reads the clamp area from the switches 57 and 58 which determine the display 56. The setting of the multi-way switch 52 tells the system whether a set flow or a set pressure difference is to be used in the measurement, and which of two values the flow or pressure difference is to be. The microprocessor system 28 then reads internally a present group of switches the setting of which represents a value between 0 and 1 and will be referred to hereinafter as FRAC. This value is the fraction of the set value of flow or pressure difference at which a first measurement is to be attempted. The range of measurements taken extends above the set value by the same amount as this fraction is below the set value. The system 28 then internally reads another group of preset switches which encode a number referred to hereinafter as STEPS which is the number of steps or measurements to be utilized in curve fitting. This number is an odd integral number which is at least 3.

The intended values at which measurements are to be taken are calculated by the system 28 from an equation which, in the case of pressure difference, is as follows:

$$P(K) = P \times \left[ FRAC + \frac{(1-FRAC)}{\frac{(STEPS-1)}{2}} \times (K - 1) \right]$$

where K is the number of the step concerned, and is therefore equal to any whole number from 1 to the number STEPS. This equation is used by the system 28 if the multi-way switch 52 is set to a position indicating that porosity at a set clamp pressure is to be determined. If the switch 52 indicates that the porosity is to be determined at a set value of flow, a similar equation in which P (K) is replaced by flow value F (K) and P, which represented a set value of pressure difference, is replaced by F representing a set value of flow is used.

If a set pressure difference is required, the system 28, on sensing that the start button 66 has been pressed, attempts to set the clamp pressure sensed at the port 36 of the valve 34 at the first value determined by the above equation for P (K) by operating the motor 27 to control the flow controller 25, stops the motor 27 when the sensed pressure difference appears correct, reads the actual steady values of pressure at the two ends of the restrictor 30 relative to atmosphere so as to determine the values of flow and clamp pressure differential at the current value of K, then increments the value of K by 1 and repeats the process. This cycle is repeated until the value of K reaches the value of STEPS. The system 28 then fits a curve to the pairs of flow and pressure difference values obtained by the measurements by using a method of least squares. Values for A and N are thus obtained for the equation $F = A (P)^N$. Then, the switch 52 being set to a pressure indication, the system 28 calculates a value of F from the calculated values of A and N and the chosen set value of P determined by the position of the multi-way switch 52. These two values of F and P are then inserted in a porosity equation by the system 28, the equation being as follows:

Porosity = $F$ (ml/sec) $\times 60 \times$ (1/clamp area) $\times 101.7/P$(mmW.G.)

i.e. in units of ml/min/sq.cm./centibar

To cause the system 28 to carry out its calibrate mode of operation, the system 28 is switched on, the ready button 64 is pushed and then the calibrate button 65 is pushed. On subsequently pushing the start button 66, the system 28 senses that the calibrate button 65 has been pushed, and reads the multi-way switch 52' to establish what factors are to be calculated. In this mode of operation, only three settings of the switch 52' are used, these being the settings 52, 53, and 54, which in this mode represent respectively calibrate transducer 42, calibrate transducer 43, and calibrate restrictor 30. In calibrating the transducers 42 and 43, a manometer (not shown) is connected in communication with that end of the restrictor 30 which communicates with the outlet 29 of the flow controller 25. This enables the actual pressure relative to atmosphere at the outlet 29 to be measured. The system 28 proceeds by setting the pressure at the outlet 29 to 10 mm water gauge or 100 mm water gauge depending upon whether the high sensitivity or low sensitivity transducer is being calibrated, the valves 34 and 39 being suitably set to provide communication between the outlet 29 and both transducers. The system 28 then displays the sensed pressure at the display 59 if it is the low sensitivity transducer which is being calibrated. The displayed value is then adjusted by manual setting of the switches 61 until the displayed value is in agreement with the manometer value. This adjustment calibrates the low sensitivity transducer. If it is the high sensitivity transducer which is being calibrated, the sensed value of pressure is displayed at the display 60, and is brought into agreement with the manometer value by manual setting of the switches 62. This calibrates the high sensitivity transducer.

If the setting of the multiway switch 52' indicates that the restrictor 30 is to be calibrated, instead of a manometer being connected to the inlet end of the restrictor 30, the clamp 31 is removed and replaced with a spirometer or other flow measuring instrument capable of measuring flow accurately within the range possible for the equipment. The system 28 on reading the switch 52' as indicating calibration of the restrictor 30 senses the pressure difference across the restrictor 30 and displays the computed flow at the display 60. The displayed flow value is then adjusted by manual setting of the switches 63 to bring the displayed value into agreement with the value indicated by the flow measuring instrument communicating with the outlet end of the restrictor 30.

Figure 9A:
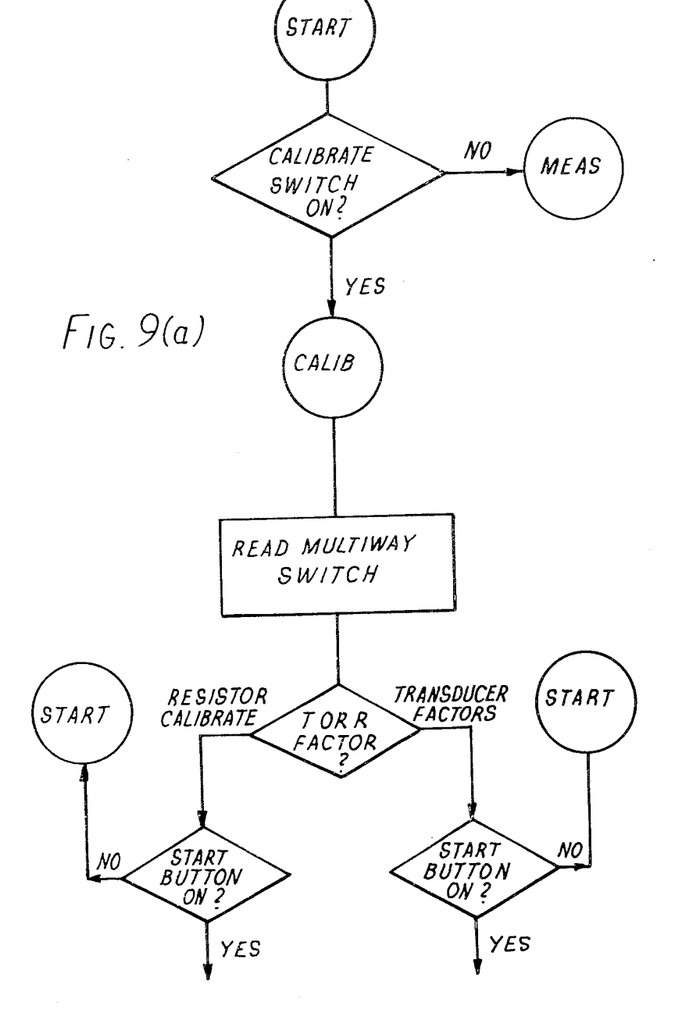
Figure 9B:
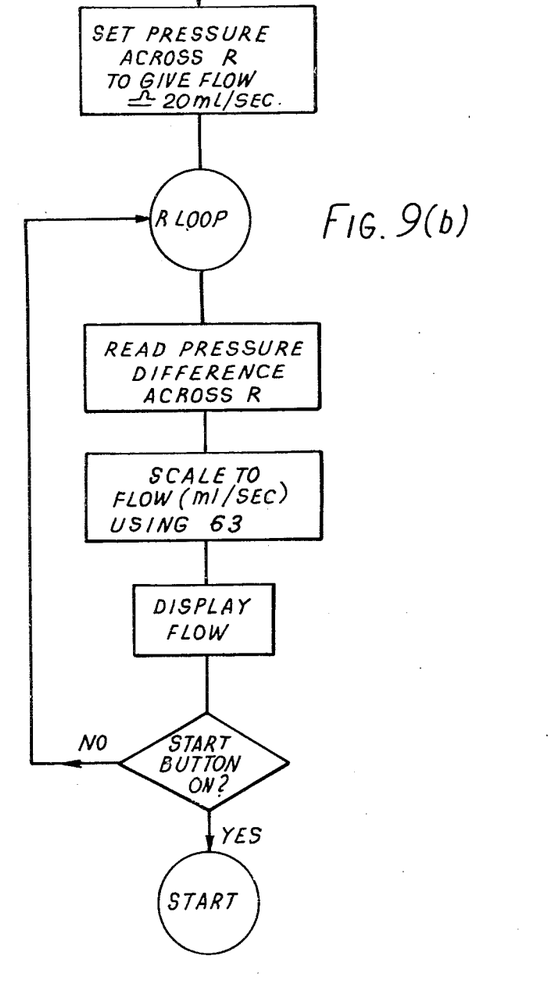
Figure 9C:
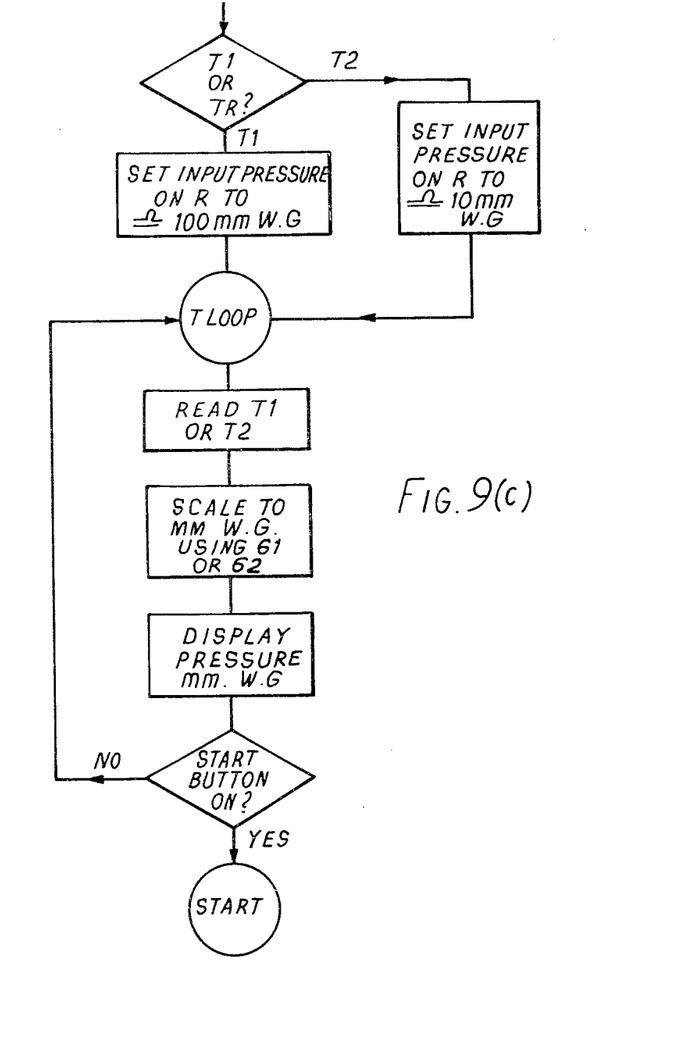
Figure 10A:
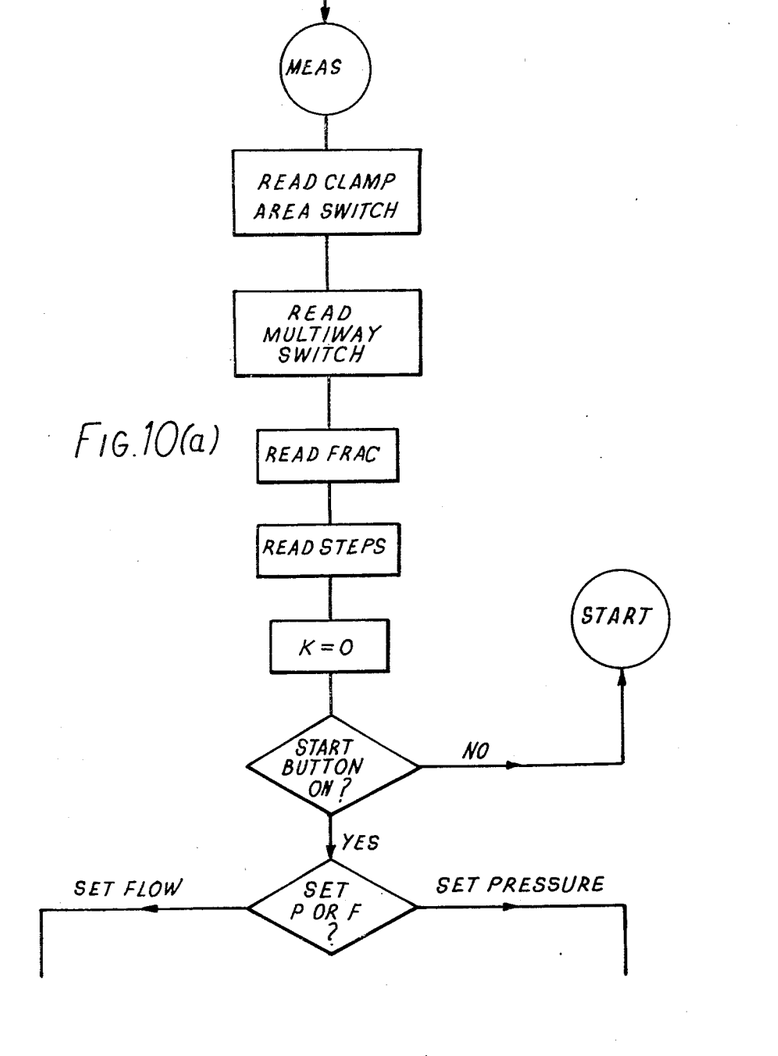
Figure 10B:
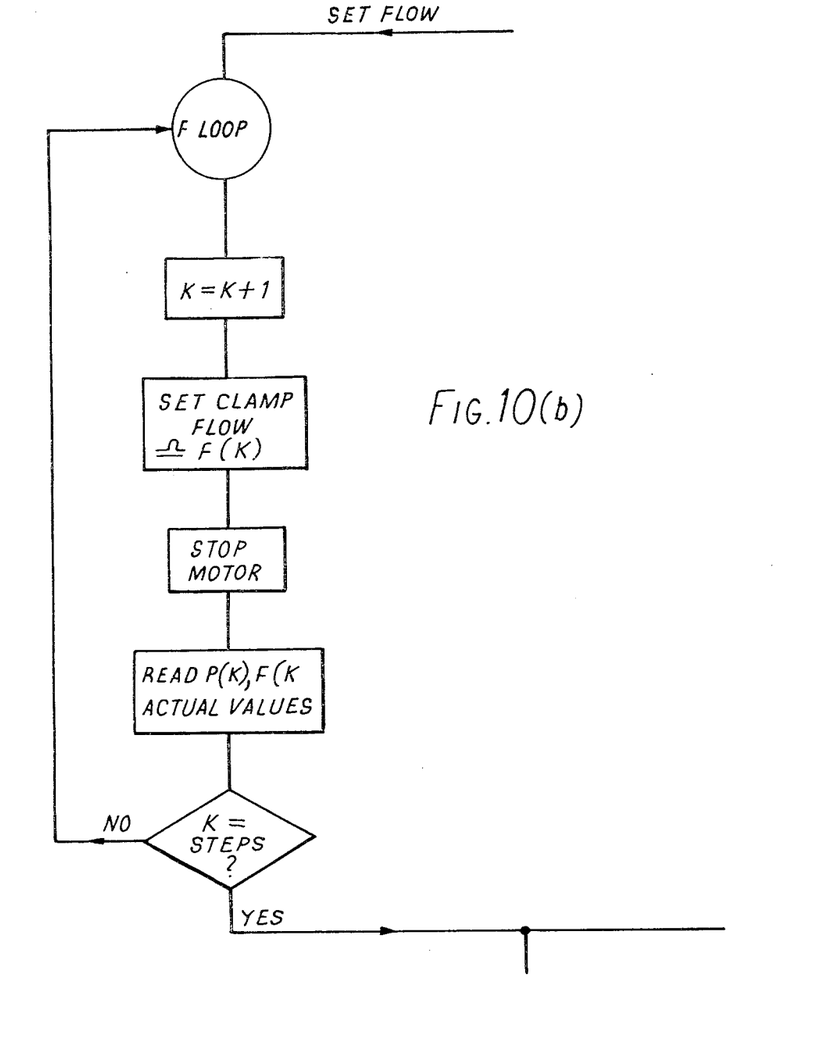
Figure 10C:
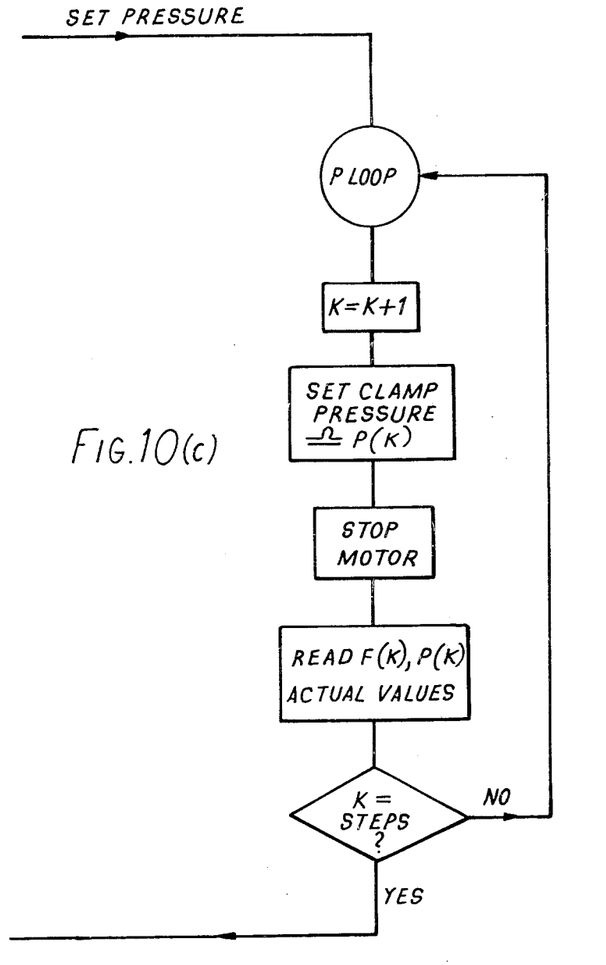
Figure 10D:
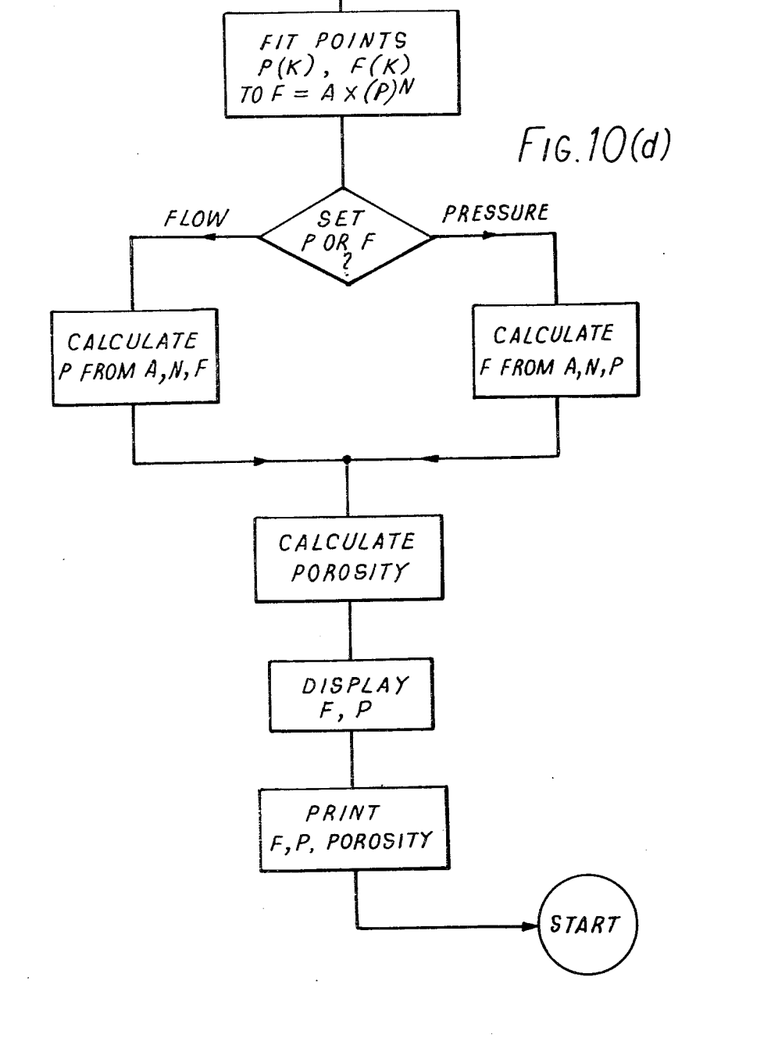

FIGS. 9 and 10 are the flow diagrams of the calibrate and measurement modes of operation of the system 28.

A suitable algorithm for the least squares method of fitting a curve is described in Numerical Methods and Fortran Programming, by McCracken and Dorn, published by John Wiley and Sons, Inc., August, 1968, pages 262-266.

We claim:

1. A method of measuring the porosity of a sheet material to a gas at a given flow rate of the gas through the sheet material which comprises automatically setting the flow rate of the gas through the sheet material at a number of values close to said given value, measuring the value of the pressure drop through the sheet material at each of said close flow rate values, calculating from said close and measured values the values of constants A and N for said sheet material in the equation:

$$\text{flow rate} = A \times (\text{pressure drop})^N;$$

from these calculated values of A and N for the sheet material calculating the pressure drop through the material at said given flow rate, and calculating the porosity with the given flow rate and the calculated pressure drop, the automatic setting of the flow rate at said close values, the calculation of A and N, and the calculation therefrom of the pressure drop at the given flow rate and the porosity being achieved by means of a microprocessor.

2. A method of measuring the porosity of a sheet material to a gas at a given pressure drop of the gas through the sheet material which comprises automatically setting the pressure drop of the gas through the sheet material at a number of values close to said given value, measuring the value of the flow rate through sheet material at each of said close pressure drop values, calculating from said close and measured values the values of constants A and N for said sheet material in the equation $$\text{flow rate} = A \times (\text{pressure drop})^N$$

from these calculated values of A and N for the sheet material calculating the flow rate through the material at said given pressure drop, and calculating the porosity with the given pressure drop and the calculated flow rate, the automatic setting of the pressure drop at said close values, the calculation of A and N, and the calculation therefrom of the flow rate at the given pressure drop and the porosity being achieved by means of a microprocessor.

3. Apparatus for use in measuring the porosity of a sheet material to a gas at a given flow rate of the gas through the sheet material, which apparatus comprises clamp means for holding at least a portion of the sheet material and defining a gas flow path therethrough of predetermined area, a controllable gas source, means defining a gas flow route from the controllable gas source to the clamp means, and transducing means operable to sense the gas flow rate in the gas flow route and the pressure drop across the clamp, wherein a microprocessor is operatively connected to the controllable gas source and transducing means and operable automatically to set the flow rate of the gas in the gas flow route at a number of values close to said given value, to calculate from the said close flow rate values and the corresponding sensed values of the pressure drop across the clamp the values of constants A and N for said sheet material in the equation:

$$\text{flow rate} = A \times (\text{pressure})^N$$

and to calculate from these calculated values of A and N the pressure drop across the clamp at said given flow rate, and the porosity with the given flow rate and the calculated pressure drop.

4. Apparatus according to claim 3, wherein the controllable gas source includes a controllable flow regulator.

5. Apparatus for use in measuring the porosity of a sheet material to a gas at a given pressure drop of the gas through the sheet material, the apparatus comprising clamp means for holding at least a portion of the sheet material and defining a gas flow path therethrough of predetermined area, a controllable gas source, means defining a gas flow route from the controllable gas source to the clamp means, and transducing means for sensing the gas flow rate through the gas flow path and the pressure drop across the clamp, wherein a microprocessor is operatively connected to the controllable gas source and transducing means and operable automatically to set the pressure drop of the gas across the clamp at a number of values close to said given value, to calculate from the said close values and the corresponding sensed values of the gas flow rate the values of constants A and N for said sheet material in the equation:

$$\text{flow rate} = A \times (\text{pressure drop})^N$$

and to calculate from these calculated values of A and N the flow rate at the said given pressure drop, and the porosity with the given pressure drop and the calculated flow rate.

6. Apparatus for measuring the porosity of a sheet material to a gas, the apparatus comprising clamp means for holding at least a portion of the sheet material and defining a gas flow path therethrough of predetermined area, a controllable gas source, means defining a gas flow route from the controllable gas source to the clamp means, a gas flow restrictor in the gas flow route and having a known relationship of gas flow therethrough to pressure drop therethrough, transducing means for sensing the pressure drop across the restrictor and across the clamp, and a microprocessor operatively connected to the controllable gas source and the transducing means and operable automatically (a) to set the controllable gas source to provide gas flow in the gas flow route at a number of values close to a given value at which the porosity of the sheet material to the gas is to be measured, (b) to calculate the said close gas flow values from the sensed pressure drop values through the restrictor and the known gas flow to pressure drop relationship of the restrictor, (c) to calculate from the thus obtained flow rate values and the corresponding sensed pressure drop values across the clamp the values of constants A and N for said sheet material in the equation:

$$\text{flow rate} = A \times (\text{pressure drop})^N$$

(d) to calculate from these calculated values of A and N the pressure drop across the clamp at the said given flow rate.

7. Apparatus according to claim 6, wherein said transducing means comprises a first transducer connected across the restrictor and a second transducer connected across the clamp means.

8. Apparatus according to claim 6, wherein the transducing means has independently operable modules of different sensitivities and wherein the apparatus includes means for selecting the appropriate module according to the gas flow rates and pressure drops to be encountered.

9. Apparatus according to claim 6, wherein the controllable gas source includes a controllable flow regulator adapted to be controlled by the microprocessor.

10. Apparatus according to claim 9, wherein the transducing means comprises a pair of transducers of different sensitivites arranged to supply pressure data to the microprocessor, the microprocessor being adapted to select the data received from either transducer.

11. Apparatus according to claim 10, wherein electrically controlled valves arranged to be controlled by the microprocessor are provided for selectively coupling the transducers to the inlet and outlet ends of the said restrictor.

12. Apparatus for measuring the porosity of a sheet material to a gas, the apparatus comprising clamp means for holding at least a portion of the sheet material and defining a gas flow path therethrough of predetermined area, a controllable gas source, means defining a gas flow route from the controllable gas source to the clamp means, a gas flow restrictor in the gas flow route and having a known relationship of gas flow therethrough to pressure drop therethrough, transducing means for sensing the pressure drop across the restrictor and across the clamp, and a microprocessor operatively connected to the controllable gas source and transducing means and operable automatically (a) to set the controllable gas source to provide pressure drop values across the clamp at a number of values close to a given value at which the porosity of the sheet material to the gas is to be measured,
(b) to calculate the corresponding gas flow values from the sensed pressure drop values through the restrictor and the known gas flow to pressure drop relationship of the restrictor,
(c) to calculate from the thus obtained flow rate values and the corresponding sensed pressure drop values across the clamp the values of constants A and N for said sheet material in the equation:

$$\text{flow rate} = A \times (\text{pressure drop})^N$$

(d) to calculate from these calculated values of A and N the flow rate through the clamp at the said given value.

13. Apparatus according to claim 12, wherein said transducing means comprises a first transducer connected across the restrictor and a second transducer connected across the clamp means.

14. Apparatus according to claim 12, wherein the transducing means has independently operable modules of different sensitivities and wherein the apparatus includes means for selecing the appropriate module according to the gas flow rates and pressure drops to be encountered.

15. Apparatus according to claim 12, wherein the controllable gas source includes a controllable flow regulator adapted to be controlled by the microprocessor.

16. Apparatus according to claim 15, wherein the transducing means comprises a pair of transducers of different sensitivities arranged to supply pressure data to the microprocessor, the microprocessor being adapted to select the data received from either transducer.

17. Apparatus according to claim 16, wherein electrically controlled valves arranged to be controlled by the microprocessor are provided for selectively coupling the transducers to the inlet and outlet ends of the said restrictor.

* * * * *